United States Patent [19]
Folkman et al.

[11] Patent Number: 5,096,892
[45] Date of Patent: Mar. 17, 1992

[54] ARYLSULFATASE INHIBITION AND POTENTIATION OF ANGIOSTATIC STEROIDS AND HEPARIN

[75] Inventors: Moses J. Folkman, Brookline; Neil T. Chen, Newton Center; Elias J. Corey, Cambridge, all of Mass.

[73] Assignees: The Children's Medical Center Corporation, Boston; President and Fellows of Harvard College, Cambridge, both of Mass.

[21] Appl. No.: 199,620

[22] Filed: May 27, 1988

[51] Int. Cl.⁵ .................. A61K 31/235; A61K 31/56; A61K 31/57; A61K 31/725
[52] U.S. Cl. ........................................ 514/56; 514/26; 514/171; 514/544; 514/709; 514/730
[58] Field of Search ................. 514/56, 171, 544, 709, 514/730, 26

[56] References Cited

U.S. PATENT DOCUMENTS

| | | | |
|---|---|---|---|
| 4,460,368 | 7/1984 | Allison et al. | 604/896 |
| 4,771,042 | 9/1988 | Braughler et al. | 514/171 |
| 4,788,307 | 11/1988 | Lormeau et al. | 536/21 |

OTHER PUBLICATIONS

Smith et al; Biochem. Pharmacol., 25:2171-2177 (1976).
The Merck Index; Ed. M. Windholz, pp. 4538-4539 (1983), Merck & Co., Inc., Rahway, N.J.
Folkman et al; Science 221:719-725 (1983).
Zucker-Franklin et al; Biochem. Biophys. Res. Commun. 126(1):540-3 (1985).
Ingber et al; Endocrinology 119(4):1768-1775 (Oct. 1986).
Chen et al; Lab. Invest. 59(4):453-459 (1988).
Chem. Abstracts (1985) 102:181218v.
DuBois et al. (1973) Biochem. and Biophys. Res. Comm. 50:1129-1135.

Primary Examiner—Ronald W. Griffin
Assistant Examiner—Nancy S. Carson

[57] ABSTRACT

Anigiogenesis is controlled by administering to a mammal an effective amount of an inhibitor of arylsulfatase. Preferably, the arylsulfatase inhibitor is administered in a pharmaceutically acceptable vehicle in combination with an angiostatic steroid and (optionally) heparin (by which term we include all forms and fragments of heparin having the desired angiostatic activity). Hydrocortisone is one specifically preferred steroid. The preferred arylsulfatase inhibitor is a carboxylic acid ester or a sulfuric acid ester of a benzylic alcohol, most preferably the esters defined more particularly below. The arylsulfatase inhibitor is preferably administered locally to the tissue experiencing undesired angiogenesis. Arylsulfatase inhibitor and an angiostatic steroid are included in a pharmaceutically acceptable vehicle, preferably also with heparin, to yield an angiostatic therapeutic composition. Also, coagulation of blood is inhibited by adding a composition comprising an arylsulfatase inhibitor and heparin to the blood. Such compositions are also disclosed.

20 Claims, 2 Drawing Sheets

ARYLSULFATASE INHIBITION AND POTENTIATION OF ANGIOSTATIC STEROIDS AND HEPARIN

BACKGROUND OF THE INVENTION

This invention was supported in part by the United States Government (USPHSRO1- CA37395) and the Government has certain rights in the invention.

This invention relates to the general field of controlling angiogenesis—i.e., preventing or treating undesired angiogenesis.

Various diseases are angiogenesis-dependent, i.e., they are related to the process by which new capillary blood vessels are formed. Uncontrolled and rampant capillary growth can cause extensive tissue damage, e.g. in diabetic retinopathy where neovascularization in the retina may lead to blindness and in rheumatoid arthritis where new vessels in the joint may destroy articular cartilage. Moreover, the progressive growth of tumors generally depends upon continuous induction of angiogenesis by the tumor.

Folkman, "Tumor Angiogenesis" in *Advance in Cancer Research*, Vol. 43, pp. 175-203 (Klein and Weinhouse, Eds.) generally reviews efforts to find angiogenesis inhibitors which might be used therapeutically, in an effort to control angiogenesis-dependent diseases. Specifically, mixtures of cortisone (or hydrocortisone) and heparin (or heparin fragments) inhibit angiogenesis, as measured by regression of growing capillaries in chick embryo, cessation of tumor-induced capillary growth in rabbit cornea, and regression of some tumors in mice. Folkman et al. *Science* 221:719 (1983). This anti-angiogenic activity is not dependent upon the anticoagulant activity of heparin, nor upon the glucocorticoid or mineralocortocoid activity of steroids. Crum and Folkman, *J. Cell Biol.* 99:158a, Abstr. #581,(1984); and Crum et al. *Science* 230:1375 (1985). The same effect is observed with several natural and synthetic steroids, and they appear to act by inducing basement membrane breakdown, endothelial cell rounding, and capillary retraction. Ingber et al. *Endocrinology* 119:1768 (1986). Heparin or heparin-like molecules are known to be present on the surface of vascular endothelial cells Buonassi et al. *Biochem. Biophys. Acta* 385:1 (1975); and Castellot et al. *J. Biol. Chem.* 257:11256 (1982). The anticoagulant and antilipidemic functions of heparin depend on the number and position of heparin sulfate groups. Danishefsky *Fed. Proc.* 36:33 (1977); Levy and Petracek *Proc. Soc. Exp. Biol. Med.* 109:901 (1962); and McDuffie "*Heparin: Structure, Cellular Function and Clinical Applications*", p. 167, Academic Press Inc., N.Y. 1979.

SUMMARY OF THE INVENTION

We have discovered that a certain class of compounds, known as sulfatase inhibitors, will potentiate the angiostatic activity of steroids. We do not wish to be bound to a specific mechanism, but it appears that sulfatase activity is endogenous to the mammal in question, and that the inhibitor inhibits desulfation of heparin components, particularly heparin and heparan sulfate present on the surface of vascular endothelial cells and in the extracellular matrix beneath endothelial cells. The desulfated heparin shows reduced angiostatic activity in combination with angiostatic steroids, thus reducing the effectiveness of steriod-heparin compositions, particularly where the heparin dosage is limiting.

Accordingly, one aspect of the invention features a method for controlling angiogenesis in a mammal by administering to the mammal an effective amount of an inhibitor of arylsulfatase. Preferably, the arylsulfatase inhibitor is administered in a pharmaceutically acceptable vehicle in combination with an angiostatic steroid and (optionally) heparin (by which term we include all forms and fragments of heparin having the desired angiostatic activity). Suitable angiostatic steroids include those described by Ingber et al. (cited above) and by Crum et al. (cited above). Hydrocortisone is one specifically preferred steroid. The preferred arylsulfatase inhibitor is a carboxylic acid ester of a benzylic alcohol or a toluenesulfonate, most preferably the esters and toluenesulfonates defined more particularly below. The arylsulfatase inhibitor is preferably administered locally to the tissue experiencing undesired angiogenesis.

A second aspect of the invention features a composition of matter for use in the above method, comprising an arylsulfatase inhibitor and an angiostatic steroid as described above, in a pharmaceutically acceptable vehicle. The composition preferably includes heparin.

A third aspect of the invention features the recognition that arylsulfatase inhibitors potentiate the anticoagulation effect of heparin (which term includes all forms and fragments of heparin with anti-coagulating ability). Specifically, this aspect of the invention features a method of inhibiting coagulation of blood (e.g. in vitro) by adding a composition comprising an arylsulfatase inhibitor and a heparin to the blood. The invention also features the anticoagulant composition. Other features and advantages of the invention will be apparent from the following description of the preferred embodiment and from the claims.

DESCRIPTION OF THE PREFERRED EMBODIMENTS

We describe first the preferred angiostatic compositions and methods; then we describe the anticoagulation feature of the invention.

DRAWINGS

ANGIOSTATIC METHODS AND COMPOSITIONS

Figure 1A:
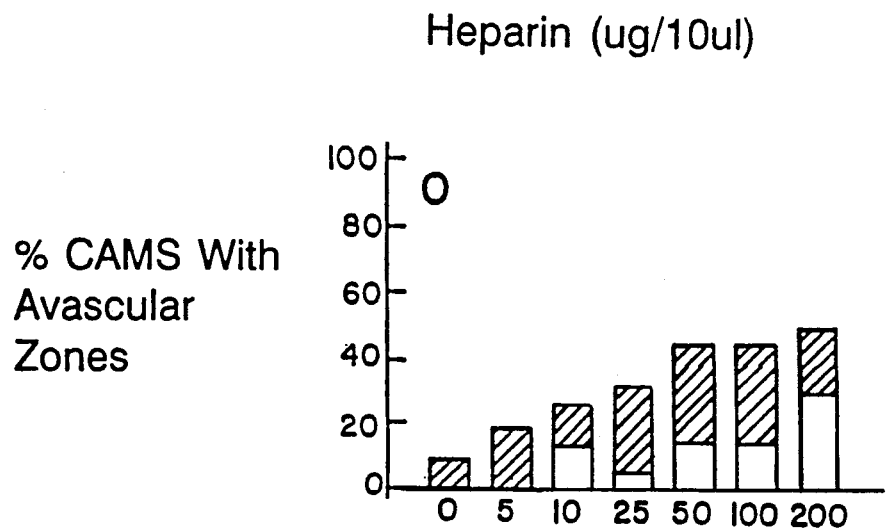
FIGS. 1a-1c are bar graphs demonstrating anti-angiogenic activity of arylsulfatase inhibitor at varying heparin concentrations.

The preferred angiostatic composition comprises an arylsulfatase inhibitor and an angiostatic steroid, as described below.

The arylsulfatase inhibitor is preferably an analog of a natural substrate of arylsulfatase, particularly esters of benzylic alcohols and toluenesulfonates. Particularly, preferred compounds are those represented by the following formula:

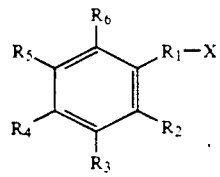

where $R_1$ is a $C_1$ or $C_2$ alkylene group, X is —O—CO—$R_7$ or —$SO_3$, $R_2$-$R_6$ are independently selected from the group consisting of H, alkyl, nitro, and hydroxyl functions and $R_7$ is an alkyl group. (preferably $C_5$ or less). In particular $R_1$ is $CH_2$, $R_2$ is OH, $R_5$ is $NO_2$, and X is —$SO_3$. Particularly suitable inhibitors are analogs of the substrate p-nitrocatechol sulfatase. One such analog is sodium 2-hydroxy-5-nitro-alpha-toluene sulfonate (HNT).

Compounds described above can be screened for the ability to block the activity of an arylsulfatase, such as commercially available arylsulfatase purified from limpets (Sigma, St. Louis), or arylsulfatase activity of chick chorioallantoic membrane. Other arylsulfatases suitable for screening inhibitors include arylsulfatase in NK cells or commercially available abalone-derived arylsulfatase. See Zucker-Franklin et al. (1985) *Biochem. Biophys. Res. Commun.* 126:540.

An optional confirmatory test of inhibitory activity includes the ability to inhibit hydrolysis of heparin by a mammalian arylsulfatase, e.g. by measuring the effect of the inhibitor on the clotting time of heparinized blood as described below.

In addition to the arylsulfatase inhibitor, the preferred angiostatic composition includes an agiostatic steroid. Preferred angiostatic steroids are those described in Crum et al. *Science* 230:1375 (1985) and Ingber et al. *Endocrinology* 119:1768 (1986), including cortisone, epicortisol, hydrocortisone, tetrahydrocortisone S, 17 α-hydroxyprogesterone, cortexolone, corticosterone, desoxycorticosterone, hydrocortisol, 6 α-fluororo-7,21-dihydroxy-16β-methylpregna-4,9-(11)-dione-3,20-dione; 11 α-hydrocortisone, 11-desoxycortisol, and 4,9(11) pregnadien-17α, 21 diol-3,20 dione. Other angiostatic steroids are listed in Table I.

Heparin can also be added to the composition. Heparin, an α, β glycosidically linked highly sulfated copolymer of uronic acid and glucosamine, has been used clinically as an anticoagulant for half a century. Despite its importance and widespread use, both the exact structure of heparin and the precise nature by which it acts in blood anticoagulation have not been elucidated. Much of the difficulty in determining the structure of heparin is because it is not a homogeneous substance. Heparin is polydisperse with a molecular weight range from 5,000 to 40,000. Within a given chain, there are also structural variations such as varying degrees of sulfation, N-acetylation, and C-5 epimerization in the uronic acid residue.

Consequently, the precise composition of commercial heparin varies depending on its source and method of purification. Heparin has been degraded by treatment with heparinase (an enzyme of bacterial origin, Langer et al., U.S. Pat. No. 4,341,869) which cleaves the molecule at the α-glycosidic linkages between N-sulfated-D-glucosamine 6-sulfate and L-iduronic acid 2-sulfate to form fragments including disaccharide, tetrasaccharide, hexasaccharide, and larger oligosaccharides, each being simply a chain-shortened heparin fragment with minor end group modification (the degradation results in a Δ-4,5 site of unsaturation in the terminal uronic acid residue). Linhardt et al., *J. Biol. Chem.*, Vol. 257, 7310-13 (1982) By the term "heparin", we mean to include all forms of heparin, and all fragments of heparin having angiostatic effect. See generally Folkman et al., *Science* 221:719-725 (1983). We specifically mean to include heparin fragments which are hexasaccharides or larger, or analogous compounds having one of the following structures:

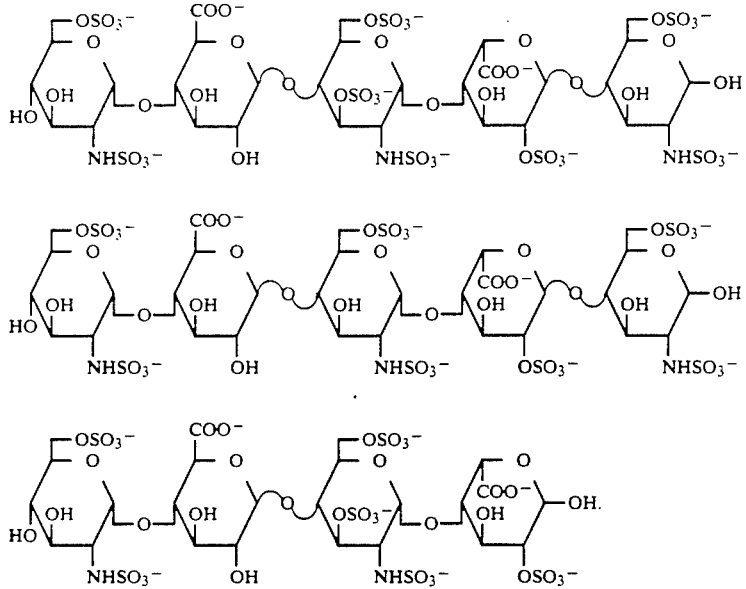

In the preferred composition, the above active ingredients are formulated with a physiologically acceptable carrier, depending on the condition being treated and the route of administration. The arylsulfatase inhibitor is present in a concentration of 5 μg/10 μl-200 μg/10 μl depending on its inhibitory activity ($k_i$, described below) its lifetime, and the route of administration.

In the present invention, a free form or a salt of arylsulfatase inhibitor may be used. As the salt, inorganic salts such as alkali metal salt, e.g. sodium salt, potassium salt, alkaline-earth metal salt, e.g. calcium salt, and ammonium salt may be exemplified.

On the basis of their strong angiogenesis inhibitory activity, arylsulfatase inhibitors are useful for prophylaxis and treatment of diseases in the fields of ophthalmology, dermatology, pediatrics, surgery and cardiology.

Thus, arylsulfatase inhibitors may be used for prophylaxis and treatment of neovascularization in diabetic retinopathy, retrolental fibroplasia, corneal graft neovascularization, neovascular glaucoma, ocular tumors, and trachoma; dermatological psoriasis and pyogenic granuloma; childrens hemangioma, angiofibroma and hemophiliac joints; and hypertrophic scars, would granulation, vascular adhesions, rheumatoid arthritis, scleroderma and atherosclerotic plaque.

The preferred arylsulfatase inhibitory compositions are low in toxicity and safely administered orally or parenterally to mammals (e.g. rat, rabbit, monkey man) in forms of e.q. tablets, granules, capsules, injectable solutions, topical creams, and eye-drops.

To treat diabetic retinopathy, for example, an arylsulfatase inhibitor composition can be administered orally or intravenously in the form of a pharmaceutical composition.

Alternatively, arylsulfatase inhibitor especially as a salt, can be administered in the form of eye-drops, i.e one to a few drops per dose can be instilled in the eye with a frequency of 1 to about 4 times a day according to the patient's condition.

For oral administration, 5 mg to 100 mg of the arylsulfatase inhibitor or its salts can be formulated as a tablet or a capsule together with carrier, diluent or vehicle.

For eye-instillation, a arylsulfatase inhibitor salt can be dissolved in distilled water to make a concentration of 0.5 mg/ml to 5 mg/ml (w/v); the solution may also contain an isotonizing agent, a preservative, or a thickening agent and is adjusted to pH 5 to 9.

EXAMPLE 1

Screening Inhibitors

By way of example, and not as a limitation, the following experiments demonstrate the protocol for screening inhibitors, using the natural substrate, p-nitrocatechol sulfate and arylsulfatase from the chick choriollantoic membrane. Specifically, arylsulfatase activity is measured, with and without the inhibitor.

As described below in detail, the activity of arylsulfatase in the chorioallantoic membrane was measured with the substrate p-nitrocatechol sulfate, using the extinction coefficient of the product p-nitrocatechol in 1N NaOH using 12670 $M^{-1}$). The specific activity of the arylsulfatase in the membrane was 0.015 U/mg protein when bovine serum albumin was used as a protein standard. One unit of activity is that amount of enzyme sufficient to hydrolyze 1 $\mu$M of sulfatase per hour.

An homogenate of chorioallantoic membrane was prepared by pooling ten 8-day old chorioallantoic membranes which had been excised from the rest of the embryo and rinsed in 0.9% NaCl at 4° C. to remove blood and amniotic fluid. The membranes were transferred to a glass homogenizer in 2 ml of iced sodium-acetate buffer (0.2M, pH 5.0) which also contained 0.1M ethylenediamine tetra-acetate. The membranes were homogenized manually and then sonicated (VibraCell, Sonics and Materials, Danbury, Conn.) until no intact cells were identified by microscopic examination. The homogenate was then centrifuged and the supernate collected for enzymatic assays.

P-nitrocatechol sulfate (Sigma Chemical Company, St. Louis, Mo.) was dissolved in 0.2M acetate buffer (pH 5.0) to yield a 6.25 mM solution. In a test tube, 200 ul or 0.2M acetate buffer, 160 ul of the p-nitrocatechol solution, and 40 ul of the sample were mixed and incubated at 37° C. for 30 minutes. The reaction was quenched by addition of 1N NaOH (2 ml) which also developed the color of the product, p-nitrocatechol. The blank was prepared similarly, except that NaOH was added immediately after mixing the sample and the substrate. Absorbance at 515 nm was measured with a Beckman DU-6 spectrophotometer (Beckman Instrument, Inc., Irvine, Calif.). The extinction coefficient of p-nitrocatechol was calculated from its absorption at 515 nm p-nitrocatechol (Aldrich, Milwaukee, Wis.) at various concentrations.

To measure the ability of candidates to inhibit, the following enzyme kinetic study can be used, yielding a value for $k_i$. The substrate (p-nitrocatechol sulfate), and solutions of potential inhibitors (in this case HNT) were prepared with the acetate (0.2M) and EDTA (0.1M) buffer adjusted to pH 5.0. The homogenate of the chorioallantoic membrane was incubated with p-nitrocatechol sulfate solution at 37° C. in the presence of various concentrations of HNT. NaOH solution was used to quench the reaction, and the absorption was read at 515 nm. The results were plotted according to Lineweaver and Berk (Lehninger, *Biochemistry* 2nd Ed. Worth Publishers, New York, N.Y. p. 195 (1975)).

The inhibitor should have a $k_i$ of at least 1.0 $\mu$M and preferably at least 5.0 $\mu$M. Using commercially available arylsulfatase from limpets (Sigma), the $k_i$ for HNT with p-nitrocatechol sulfate was 8.4 $\mu$M, where the $k_m$ for the substrate was calculated to be 0.73 mM. See Zucker-Franklin, cited above, regarding similar studies on commercially available arylsulfatase derived from abalone.

EXAMPLE 2

Inhibition of Angiogenesis

The ability of arylsulfatase inhibitors to potentiate the angiostatic effect of steroids, as demonstrated in the chick embryo choriallontic membrane assay, is shown below in an HNT/hydrocortisone system.

Hydrocortisone was held constant at an optimum concentration (50 ug/embryo) while heparin and HNT concentrations were varied independently. The ability of HNT to potentiate the inhibition of angiogenesis was inversely proportional to the concentration of added heparin. In other words, HNT potentiation was greater at lower concentrations of heparin, but HNT did not potentiate optimal concentrations of heparin. In the presence of hydrocortisone, HNT inhibited angiogenesis in a dose-dependent fashion without the addition of exogenous heparin. Neither HNT alone (i.e., up to 200 $\mu$g/embryo, administered in vitro, in the absence of endogenous heparin activity), hydrocortisone alone, nor heparin alone inhibited angiogenesis.

The specific assay for angiogenesis in the chick embryo choriallantoic membrane is described in detail in Crum et al. 1985, cited above, and need not be repeated here.

Figure 1B:
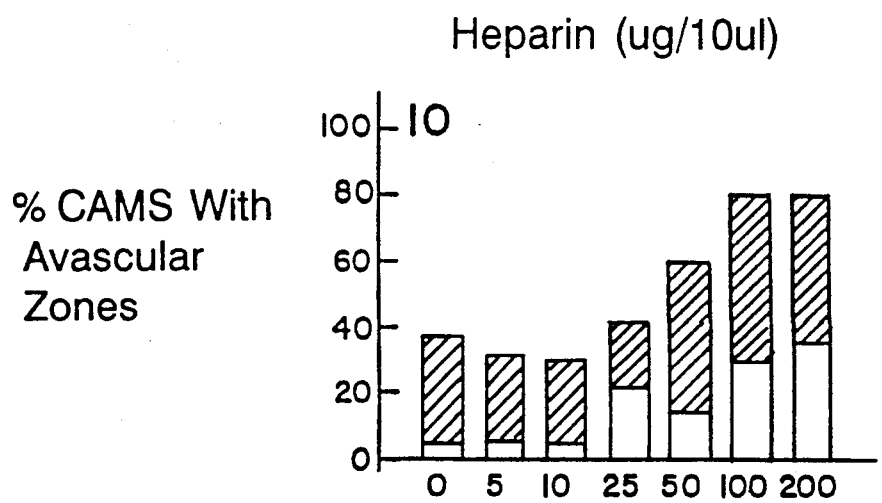
Figure 1C:
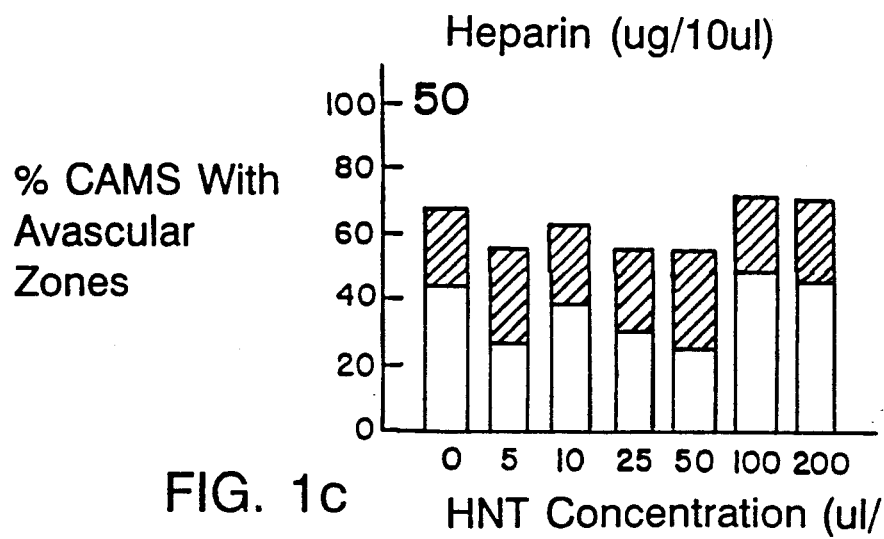

FIG. 1 demonstrates the anti-angiogenic activity of combinations of various concentrations of heparin and HNT in the presence of hydrocortisone. The black portion of each bar represents the percentage of avascular zones greater than 2 mm diameter and the hatched area represents avascular zones equivalent to 2 mm diameter. Each methylcellulose disk also contains 50 ug of hydrocortisone, one methylcellulose disk/embryo, approximately 16–20 embryos/bar. (a) No heparin present. The anti-angiogenic activity is positively correlated with a concentration of HNT p=less than 0.0001). 50% of the chorioallantoic membranes yielded avascular zones at an HNT concentration of 200 ug/disck without the administration of heparin. (b) Heparin concentration at 10 ug/disk. Anti-angiogenic activity and HNT concentration are positively correlated (p=less than 0.000003). (c) At 50 µg/disk, there is no significant correlation between the anti-angiogenic activity and HNT concentration (p=greater than 0.26). Not shown are the following concentrations of HNT: 5 µg of heparin/disk: the correlation between anti-angiogenic activity and HNT concentration was significant at p=0.04. At a heparin concentration of 25 ug/disk, there was no significant correlation between anti-angiogenic activity and HNT concentration (p=greater than 0.3).

Control of Blood Clotting

Aryl sulfatase inhibitors can be added to blood to prolong the anti-coagulant effect of heparin. Specifically, the above-described arylsulfatase inhibitors are generally useful for this purpose. Preferably the arylsulfatase inhibitor is added in a composition that includes heparin. For example, a concentration of at least 10 µM of arylsulfatase inhibitor can be included in the standard heparin additive to be used with whole blood.

The following specific example of anti-coagulant activity of arylsulfatase inhibitor is provided by way of illustration and not as a limitation on the invention.

The activated clotting time of heparinized rabbit blood was 4.75 minutes. As the concentration of HNT in heparinized blood was increased up to 10 mM, the activated clotting time exceeded 120 minutes, representing more than a 25-fold increase over heparinized blood not treated with HNT. To determine the effect of HNT on non-heparinized blood, we carried out a separate study using clotting time (without activation by siliceous earth); an activated clotting time of non-heparinized blood was too short to measure accurately. The clotting time of non-heparinized blood was not significantly lengthened except for a minimal increase in clotting time at the highest concentration of HNT tested (10 mM). In the heparinized blood, clotting time was increased by greater than 7.5-fold in the presence of only 1 uM HNT.

Heparinized blood standing in vitro will clot eventually because platelet-derived enzymes and other enzymes in the plasma will degrade heparin. Because the clotting time of heparinized blood is increased significantly by HNT, but the clotting time of non-heparinized blood is not.

Heparin (Hepar, Franklin, Ohio, Lot PM12583, activity 160 U/mg) was administered to New Zealand white rabbits (Pine Acres, Norwell, Mass.) via the auricular vein in physiologic saline at either 80 or 160 U/kg body weight. After 20 minutes, approximately 20 ml of blood was drawn from the central artery of the ear with a #19 butterfly needle into a plastic syringe. In order to determine activated clotting time, the syringe containing heparinized blood was immersed immediately in an ice bath at 4° C. Aliqouts of 1.9 ml of the chilled blood were then added to vacutainer tubes (75×13 mm, Becton-Dickinson Co., Rutherford, N.J.) containing 12 mg siliceous earth and 0.1 ml of the various concentrations of HNT in saline. Thus, the final volume of 2.0 ml contained HNT concentrations from 0 to 10 mM (FIG. 1). The contents were mixed and timing was begun when the vacutainer tubes were placed in a constant temperature bath at 37° C. The endpoint of this assay was the time required to obtain immobilization of the blood column upon inversion of the tube. The pH of the serum was measured in each tube after clotting.

In order to determine clotting time, the blood was transferred immediately in aliquots of 2.7 ml to vacuated silicone-coated glass tubes (Monojet red-top tubes, Sherwood Medical, St. Louis, Mo.) which had been pre-warmed to 37° C. and which contained 0.3 ml of HNT-saline solution as described in FIG. 1. The final volume of 3.0 ml contained HNT concentrations of 0 to 10 mM.

To demonstrate the effect of the arylsulfatase inhibitor, HNT, on activated clotting time of heparinized blood, blood was drawn 20 minutes after a rabbit had received 160 U of heparin/kg of body weight intravenously. The time required for blood to clot in a glass-tube containing siliceous earth and HNT of a given concentration was recorded. HNT (at concentrations up to 10 mM), did not prolong the clotting of unheparinized blood.

Figure 2:
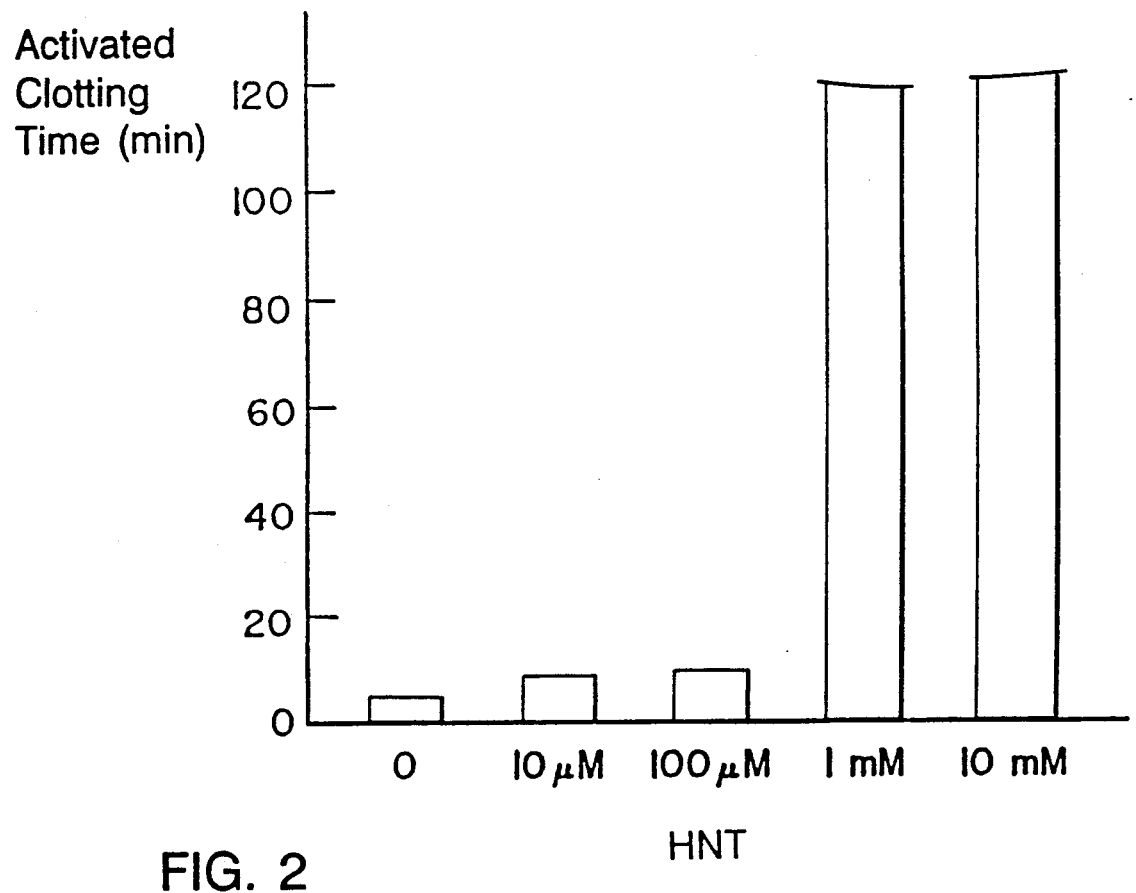
FIG. 2 is a graph demonstrating the effect of arylsulfatase inhibitor on clotting.

FIG. 2 demonstrates the effect of the arylsulfatase inhibitor, HNT, on the clotting time of heparinized blood. Blood was drawn from rabbits having either no heparinization (white bars), or 20 minutes after receiving either 80 U (hatched bars) or 160 U heparin/kg (solid bars). The clotting time was determined in silicone-coated tubes.

Other embodiments are within the following claims.

TABLE I

Angiostatic Steroids

17α,21-dihydroxy-4-pregnene-3,11,20-trione and its 21-acetate (or cortisone)

11α,17,21-trihydroxypregn-4-ene-3,20-dione (or 11α-hydrocortisone)

11β,17α,21-trihydroxypregn-4-ene-3,20-dione (or hydrocortisone)

17α,21-dihydroxypregna-4,9(11)-diene 3,20-dione

15α,17α,21-trihydroxy-4-pregnene-3,20-dione

16α,17α,21-trihydroxy-6α-methylpregn-4-ene-3,20-dione-21-acetate-16,17 cyclic ketal of acetone 6α-fluoro-17α,21-dihydroxy-16β-methylpregna-4,9(11)-diene-3,20-dione 6α-fluoro-17α, 21-dihydroxy-16β-methylpregna-4,9(11)-diene-3,20-dione-17,21-diacetate 6α,17α,21-trihydroxypregn-4-ene-3,20-dione 17α,21-dihydroxypregn-4-ene-3,20-dione-21-acetate 17α,21-dihydrcxypregn-4-ene-3,20-dione 9β,11β-epoxy-17α,21-dihydroxy-2α-methylpregn-4-ene-3,20-dione-21-acetate

We claim:

1. A method of treating angiogenesis in a mammal by administering to the mammal a therapeutically effective amount of an inhibitor of arylsulfatase, wherein said arylsulfatase inhibitor is a carboxylic acid ester of a benzylic alcohol, or a toluenesulfonate.

2. The method of claim 1 wherein said arylsulfatase inhibitors has the following formula:

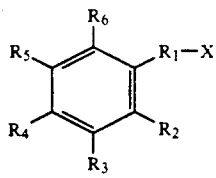

where $R_1$ is a $C_1$ or $C_2$ alkylene group, X is $-O-CO-R_7$ or $-SO_3$, $R_2-R_6$ are independently selected from the group consisting of H, alkyl, nitro, and hydroxyl functions, and $R_7$ is an alkyl group.

3. The method of claim 2 wherein $R_2$ is $-OH$, $R_5$ is $-NO_2$, and X is $-SO_3$.

4. The method of claim 3 wherein said arylsulfatase inhibitor is sodium 2-hydroxy-5-nitro-α-toluenesulfonate.

5. The method of claim 1 wherein said arylsulfatase inhibitor is administered in combination with heparin.

6. The method of claim 1 wherein said arylsulfatase inhibitor is administered locally to tissue experiencing undesired angiogenesis.

7. A composition of matter comprising an arylsulfatase inhibitor and a second compound, said second compound being an angiostatic steriod, in a pharmaceutically acceptable vehicle, said aryl sulfatase inhibitor being a carboxylic acid ester of a benzylic alcohol or a toluenesulfonate.

8. The composition of claim 9 further comprising heparin.

9. The composition of claim 7 wherein said arylsulfatase inhibitor has the following formula:

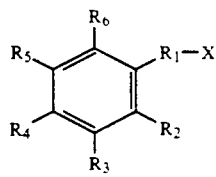

where $R_1$ is a $C_1$ or $C_2$ alkylene group, X is $-O-CO-R_7$ or $-SO_3$, $R_2-R_6$ are independently selected from the group consisting of H, alkyl, nitro, and hydroxyl functions, and $R_7$ is an alkyl group.

10. The composition of claim 9 wherein $R_2$ is $-OH$, $R_5$ is $-NO_2$, and X is $-SO_3$.

11. The composition of claim 10 wherein said arylsulfatase inhibitor is sodium 2-hydroxy-5-nitro-α-toluenesulfonate.

12. In a method of inhibiting clotting of mammalian blood comprising adding to the blood a composition comprising heparin, wherein the improvement comprises further adding an arylsulfatase inhibitor.

13. The method of claim 12 wherein the arylsulfatase inhibitor is a carboxylic acid ester of a benzylic alcohol or a toluenesulfonate.

14. The method of claim 13 wherein said arylsulfatase inhibitor has the following formula:

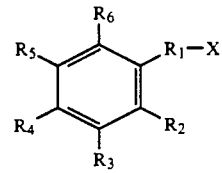

where $R_1$ is a $C_1$ or $C_2$ alkylene group, X is $-O-CO-R_7$ or $-SO_3$, $R_2-R_6$ are independently selected from the group consisting of H, alkyl, nitro, and hydroxyl functions, and $R_7$ is an alkyl group.

15. The method of claim 14 wherein $R_2$ is $-OH$, $R_5$ is $-NO_2$, and X is $-SO_3$.

16. The method of claim 15 wherein said arylsulfatase inhibitor is sodium 2-hydroxy-5-nitro-α-toluenesulfonate.

17. A composition of matter comprising an arylsulfatase inhibitor and heparin, said arylsulfatase inhibitor being a carboxylic acid ester of a benzylic alcohol or a toluenesulfonate.

18. The composition of matter of claim 16 wherein said arylsulfatase inhibitor has the follow formula:

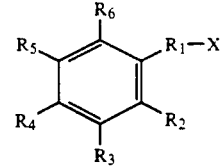

where $R_1$ is a $C_1$ or $C_2$ alkylene group, X is $-O-CO-R_7$ or $-SO_3$, $R_2 \propto R_6$ are independently selected from the group consisting of H, alkyl, nitro, and hydroxyl functions, and $R_7$ is an alkyl group.

19. The composition of matter of claim 18 wherein $R_2$ is $-OH$, $R_5$ is $-NO_2$, and X is $-NO_3$.

20. The composition of matter of claim 19 wherein said arylsulfatase inhibitor is sodium 2-hydroxy-5-nitro-α-toluenesulfonate.

* * * * *